United States Patent [19]

Rosenberg et al.

[11] Patent Number: 5,370,877

[45] Date of Patent: Dec. 6, 1994

[54] METHOD FOR IMPROVING DELIVERY AND REDUCING TOXICITY OF BIOLOGICALLY ACTIVE SUBSTANCES USING NOVEL α-AMINO DICARBOXYLIC ACID DERIVATIVES

[75] Inventors: Joerg Rosenberg; Hans-Heinrich Gruenhagen; Dieter Lenke, all of Ludwigshafen, Germany

[73] Assignee: Knoll AG, Ludwigshafen, Germany

[21] Appl. No.: 40,582

[22] Filed: Mar. 31, 1993

Related U.S. Application Data

[60] Division of Ser. No. 953,296, Sep. 30, 1992, abandoned, which is a continuation of Ser. No. 626,317, Dec. 13, 1990, abandoned, which is a continuation of Ser. No. 318,134, Mar. 2, 1989, abandoned.

[30] Foreign Application Priority Data

Mar. 3, 1988 [DE] Germany ............................. 3806852

[51] Int. Cl.$^5$ ............................................. A61K 9/127
[52] U.S. Cl. ........................................ 424/450; 264/4.1; 560/169; 560/170; 560/171
[58] Field of Search ...................... 424/450; 428/402.2; 264/4.1

[56] References Cited

FOREIGN PATENT DOCUMENTS 62-138502 6/1987 Japan .

OTHER PUBLICATIONS

Kunitake, J. Macromol. Sci., Chem., A21 (8–9), pp. 1232–1252 (1984).
Kunitake, J. Am. Chem. Soc., 103 (19) pp. 5945–5947 (1981).
Poznansky et al. Pharmacological Reviews 36 #4, p. 277, 1984.

*Primary Examiner*—G. S. Kishore
*Attorney, Agent, or Firm*—Oblon, Spivak, McClelland, Maier & Neustadt

[57] ABSTRACT

α-Aminocarboxylic acid derivatives of the formula:

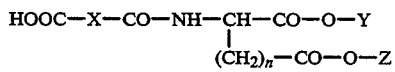

where n, X, Y and Z have the meanings stated in the description, and their preparation are described. The compounds are used in a method for improving delivery and reducing toxicity of biologically active substances by encapsulation of the biologically active substance with the above compounds.

3 Claims, No Drawings

METHOD FOR IMPROVING DELIVERY AND REDUCING TOXICITY OF BIOLOGICALLY ACTIVE SUBSTANCES USING NOVEL α-AMINO DICARBOXYLIC ACID DERIVATIVES

This application is a Division of application Ser. No. 07/953,296, filed on Sep. 30, 1992, now abandoned which is an FWC of application Ser. No. 07/318,134, filed on Mar. 2, 1989, now abandoned.

BACKGROUND OF THE INVENTION

Field of the Invention

The present invention relates to novel α-aminodicarboxylic acid derivatives, their preparation and their use as carriers for active compounds.

Discussion of the Background

In many drug preparations, the efficacy is limited in particular by the fact that the active compounds have only short half-lives in the blood and/or are subject to rapid enzymatic hydrolysis. Many active compounds also exhibit pronounced side effects as a result of unspecific absorption of these compounds in various tissue areas. In the case of other active compounds, in particular peptides and proteins, which generally cannot be administered orally, there is a need for a drug formulation which permits continuous release of the active compound into the blood stream by biodegradable drug carriers. It is known that side effects, particularly in the case of cancerostatics, can be avoided if drug carrier systems make it possible to achieve controlled transport of these active compounds to the target organ (or tumor), for example by administration in the form of biodegradable, ultrafine particles.

It is also known that vesicles (also referred to as liposomes), which have been described as a carrier system for active compounds (EP 178 624, etc.), can be formed from the naturally occurring phospholipids in water. However, such systems have some disadvantages:

(i) the lipids extracted from natural material are lipid mixtures which have a variable composition depending on the source of the raw material;
(ii) the chemical synthesis of the pure phospholipids (pure substances) is expensive;
(iii) the phospholipids are unstable, are readily oxidized or are converted into highly toxic lysolecithins by hydrolysis; and
(iv) the possibilities for the formation of vesicles having particular properties by choosing suitable lipids is restricted, owing to the limited range of pure phospholipids.

SUMMARY OF THE INVENTION

We have found that α-aminodicarboxylic acid derivatives of the formula I

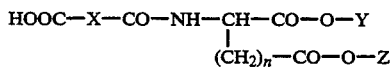

where X is $C_2$-$C_6$-alkylene, —CH=CH— or unacetylated or acetylated —$CH_2$—CHOH—, —CHOH—CHOH— or —$CH_2$—$CHNH_2$—, Y and Z are each an aliphatic hydrocarbon radical of 8 to 30 carbon atoms and n is 2 or 3, and their sodium, potassium or ammonium salts are more suitable carrier systems for active compounds.

DETAILED DESCRIPTION OF THE PREFERRED EMBODIMENTS

Examples of HOOC—X—CO groups are the radicals of fumaric acid, sebacic acid, malonic acid, glutaric acid, adipic acid, succinic acid, tartronic acid, malic acid, tartaric acid, aspartic acid and glutamic acid. Dicarboxylic esters of 4 carbon atoms which may carry one or two acetylated hydroxyl groups or an unacetylated or acetylated amino group are preferred. The succinic acid radical is very particularly preferred.

D-, L- and D,L-aspartic acid and D-,L- and D,L-glutamic acid are particularly suitable amino acid building blocks.

The groups —O—Y and —O—Z are derived from saturated or unsaturated, linear or branched fatty alcohols which have an even or odd number of carbon atoms and whose hydroxyl group may or may not be a terminal group, or which possess polymerizable groups, for example diene or diyne groups within the carbon chain and have a total length of 8 to 30 carbon atoms. Saturated or unsaturated fatty alcohols which have an even or odd number of carbon atoms, a terminal hydroxyl group and a chain length of 10 to 22 carbon atoms are preferred. The radicals of 1-dodecanol, 1-tetradecanol, 1-hexadecanol, 1-octadecanol and 9-octadecen-1-ol and 9,12-octadecadien-1-ol are very particularly preferred.

In addition to the sodium and potassium salts of the novel compounds, ammonium salts are also suitable, the ammonium salts being derived from ammonia and alkylamines where alkyl is of not more than 6 carbon atoms.

The novel compounds can be prepared by reacting an aminodicarboxylic ester of the formula II

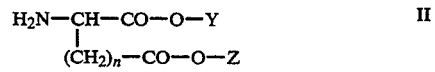

where Y, Z and n have the stated meanings, with an anhydride of a dicarboxylic acid of the formula III

where X has the stated meanings, and, if required, converting the resulting α-aminodicarboxylic acid derivative into its salts.

The reaction is advantageously carried out in the presence of a base, such as pyridine, at room temperature. After acidification, for example with hydrochloric acid, the acid I is obtained from the reaction product and can be converted into its salt using a base.

The starting compounds II are obtainable from the corresponding aminodicarboxylic acid and the alcohols YOH and ZOH.

Thus, the novel compounds can be prepared in high purity in only a few reaction stages by simple syntheses which are simple to carry out. Pure phospholipids, on the other hand, are obtainable only in more expensive, multi-stage reactions. Furthermore, the novel compounds can readily be obtained as pure enantiomers (without resolution of a racemate), for example by using the naturally occurring L-amino acids. The use of exclusively naturally occurring building blocks (amino acids, fatty acid derivatives, etc.) finally also leads to low toxicity of these biodegradable amphiphiles. Contamination with highly toxic byproducts (or hydrolysis ducts), as is frequently present in the case of the phospholipids (in the form of lysolecithins), is completely absent here.

The compounds of the present invention are amphiphilic, i.e. they possess both hydrophilic and lipophilic groups. They aggregate spontaneously in aqueous systems above a defined temperature (as a rule from 20° to 70° C.) with formation of membrane bilayers, from which, for example, vesicles having a defined size or size distribution can be formed.

The amphiphilic structure of the novel compounds is much more pronounced in the case of the salts (Na, K, NH$_4$ or NR$_4$) than in the case of the uncharged carboxylic acids.

The amphiphilic nature of the novel compounds also permits the substances to be used for the preparation of emulsions, microemulsions and gels. The membrane structures built up from the compounds consist very generally of amphiphilic aggregates in which the polar head groups of the molecules are present at the interface with an aqueous phase. These aggregates may consist not only of vesicles but, for example, also of micelles or microemulsions.

The methods for the preparation of fine or ultrafine particles in the aqueous phase from the novel compounds are in principle identical with those known for similar amphiphiles (e.g. phospholipids).

Examples of the preparation of vesicles of different sizes are the following:

Method A

A weighed amount of a finely powdered novel substance is dispersed in aqueous, isotonic and buffered sodium chloride solution with the aid of a stirrer to give a cloudy but homogeneous solution. This is then allowed to cool slowly to room temperature. In the case of mixtures of the compounds I or when, for example, cholesterol is incorporated, the weighed mixture is dissolved in a little methylene chloride or in another organic solvent. Thereafter, the solvent is removed under reduced pressure and the aqueous phase is then added, while stirring.

The resulting solution containing multilamellar vesicles can then be treated with ultrasound until the desired size of the particles (vesicles) is reached.

In another possible method for further reducing the size of the particles, the vesicle solution obtained is then forced through filter membranes having a defined pore size (pressure filtration). If desired, the process is repeated several times until the particles (vesicles) have the desired size (extrusion process).

Method B

Vesicles having a very narrow size distribution can also be formed, for example, by controlled dialysis of a mixed micelle solution of the novel compounds and suitable detergents (e.g. octylglucose or sodium cholate), with or without the aid of the apparatuses commercially available for this purpose (e.g. LIPOPREP ®). However, the detergent can also be separated from the mixed micelle solution by, for example, gel filtration.

Method C

A concentrated solution of a novel compound in an organic solvent is sprayed with the aid of a fine canula, under pressure, into a thermostated vessel filled with buffered isotonic sodium chloride solution.

Method D

Micelle-forming surfactants, e.g. ®CREMOPHOR EL (polyethoxyethylene glycerol triricinoleate) are mixed with a novel compound. Water is added to the stirred mixture, dropwise at first and then in larger portions, so that a clear mixed micelle solution forms.

The vesicles prepared according to Method A are polydisperse; the sizes are from 0.1 to 5 μm, but isolated larger and smaller vesicles are also present. The vesicles thus prepared are generally multilamellar and sufficiently large to permit direct observation under the optical microscope. They can be used, for example, in the production of depot preparations which are administered intramuscularly.

In the additional treatment with ultrasound, the vesicle sizes are reduced to a limiting value, which in the case of vesicles generally corresponds to a diameter of about 20 nanometers. These microvesicles are unilamellar, i.e. possess membranes which consist of only a single bilayer. The decrease in the particle size with increasing duration of exposure to ultrasound can be readily monitored by laser light scattering measurements.

The diameter of the vesicles can be preselected by pressure filtration of polydisperse multilamellar vesicle solutions using an appropriate membrane pore size.

The novel compounds are biodegradable and have low toxicity, even after intravenous administration. They are therefore particularly suitable for the preparation of aqueous dispersions which are stable for a long time, for the encapsulation of water-soluble substances, in particular active compounds, as solubilizers for sparingly water-soluble substances, for improving the penetration of biologically active substances through biological barriers, for controlled transport of substances to certain organs, for example the liver, the lung (also through inhalation) and the spleen, for increasing the selectivity and for reducing the toxicity of (active) compounds, for influencing the pharmacokinetics of an active compound by changing the release, distribution and removal from the systemic circulation, for protecting sensitive (active) compounds from chemical effects, from metabolization and from deactivation, and for stimulating immune reactions by administration of vesicle-encapsulated antigens.

For the preparation of vesicles in the novel compounds, the salt (Na, K, NH$_4$ and NR$_4$) are preferred to the carboxylic acids (cf, Table 1). On the other hand, the carboxylic acids can be readily used as mixtures with the salts, in order to influence the properties of the vesicles formed (phase transition temperature, fluidity of the membranes, size of the vesicles). No incompatibilities have been observed during the use of mixtures of different salts or of salts with different carboxylic acids in the formation of the vesicles. The properties of the vesicles prepared from the novel compounds depend to a great extent on the amphiphiles used. Thus, vesicles in which the phase transition temperatures of the membranes are in the range from 20° to 70° C. can readily be prepared simply by selecting suitable compounds (cf. Table 1). Furthermore, the shelf life of such vesicle solutions (at room temperature or at 4° C.) is dependent on the type or the mixture of the compound(s) used and may be, for example, more than one year.

When the vesicles are used for encapsulating water-soluble active compounds in the aqueous inner space, adequate stability of these vesicles not only in the buffer system used but also in biological fluids (for example in serum or blood in the case of intravenous injections) is essential. It is known that interactions with serum constituents in the case of phospholipid vesicles lead to very rapid release of the encapsulated content of the vesicles. This can be prevented by incorporating cholesterol in the membranes. It has been found that the addition of cholesterol (from 20 to 70 mol %) to vesicles of the novel compounds too prevents the encapsulated content from being released too rapidly. In the case of vesicles of some of the novel compounds, the addition of cholesterol also results in an improvement in the long-term stability of such preparations.

The stability of the novel preparations is demonstrated, for example, by photon correlation spectroscopy and fluorescence analysis.

The Examples which follow illustrate the invention.

EXAMPLE 1

Preparation of ditetradecyl N-(4-oxobutanoic acid)-L-glutamate a) Preparation of the starting material 88.8 g (0.6 mole) of L-glutamic acid, 256.8 g (1.2 moles) of 1-tetradecanol and 136.8 g (0.72 mole) of 4-toluenesulfonic acid monohydrate in 2,500 ml of cyclohexane were refluxed under a water separator until the calculated amount of water had distilled over. After the solvent had been evaporated off, the residue was taken up in warm ethyl acetate and the solution was carefully extracted by shaking with saturated sodium bicarbonate solution (in the case of emulsification, the mixture was heated or solid NaCl was added for salting out). Thereafter, the organic phase was evaporated down and the residue was taken up in 2,000 ml of acetone. The pH was brought to 2 at 30°-40° C. with dilute aqueous hydrochloric acid. The precipitated product was dissolved by boiling for a short time, the batch was left to stand overnight and the precipitate was filtered off under suction, washed thoroughly with cold acetone and left to dry for several days at room temperature in the air and then under reduced pressure.

Yield: 261 g (76%)

Melting point: 91°-92° C.

b) Preparation of the end product 259 g (0.45 mole) of ditetradecyl L-glutamate hydrochloride and 1,400 ml of methylene chloride were introduced into a 4 1 flask. 135 g of pyridine were added dropwise to this solution at room temperature, and a total of 54.6 g (0.546 mole) of succinic anhydride was added in two portions, while stirring, after which stirring was continued overnight. After extraction by shaking with 500 ml of a monomolar hydrochloric acid solution and 500 ml of water (twice in each case), the organic phase was dried over sodium sulfate and then evaporated down. The residue was recrystallized from methanol.

Yield: 281 g (97%)

Melting point: 68° C.

c) Conversion into the potassium salt 256 g (0.4 mole) of the reaction product from b) were dissolved in 1,200 ml of tetrahydrofuran (THF). Aqueous 5 M potassium hydroxide solution was added dropwise to the stirred solution at room temperature until the pH had reached 9-9.5, after which stirring was continued for a further hour at room temperature. The flask was then placed in ice water for one hour, after which the precipitate was filtered off under suction in a cold room (8° C.). The precipitate filtered off was washed with ice-cold THF and dried in the air.

Yield: 223 g (78%)

Melting point: 165°-167° C.

EXAMPLE 2

Preparation of dioleyl N-(4-oxobutanoic acid)-L-aspartate a) Preparation of the starting material 23.6 g (0.088 mole) of oleyl alcohol, 5.3 g (0.04 mole) of aspartic acid and 8.4 g (0.044 mole) of p-toluenesulfonic acid hydrate in 120 ml of cyclohexane were refluxed for 17 hours under nitrogen, under a water separator. The solvent was then removed under reduced pressure and the residue was taken up in ethyl acetate. The organic phase was extracted by shaking with sodium bicarbonate solution and then dried over sodium sulfate. Finally, HCl gas was passed in until the pH reached about 2 (cooling with ice). The precipitated product was filterd off under suction while cold, recrystallized from acetone and dried under reduced pressure.

Yield: 17.2 g (64%)

Melting point: 53°-55° C.

b) Preparation of the end product 16.1 g (0.024 mole) of dioleyl L-aspartate hydrochloride were dissolved in 80 ml of methylene chloride and 21 ml of pyridine. 2.9 g (0.029 mole) of succinic anhydride were added a little at a time to the stirred solution, and stirring was continued for 5 hours at room temperature. The organic phase was extracted by shaking (twice with 100 ml of 1 M HCl and three times with water) and then dried over sodium sulfate and evaporated down. The oily residue was dissolved in 150 ml of acetonitrile and was allowed to crystallize with vigorous stirring and cooling with ice. The precipitate was filtered off cold after 45 minutes and crystallized from acetonitrile, and the crystals were dried under reduced pressure.

Yield: 15.6 g (89%)

Melting point: 42°-43° C.

c) Conversion into the potassium salt 7.4 g (0.01 mole) of the reaction product from b) were dissolved in 30 ml of tetrahydrofuran. 5 N potassium hydroxide solution was added dropwise to the stirred solution, while the pH was monitored, until the pH reached 9.3, after which stirring was continued for a further hour. Acetonitrile (about 30 ml altogether) was slowly added dropwise, while stirring vigorously. Finally, the mixture was cooled to −20° C. to −30° C. and stirred for a further 30 minutes at this temperature. The precipitate which had separated out was filtered off under suction at the low temperature and washed with cold acetonitrile, and the wax-like residue was dried under reduced pressure.

Yield: 7.1 g (91%) of wax.

The following compounds of the formula I were prepared from the corresponding L-amino acids, similarly to Examples 1 and 2:

| Example No | $X^{(1)}$ | n | Y | Z | Salt/acid | m.p. (°C.) |
|---|---|---|---|---|---|---|
| 2a | 2 | 2 | $C_{14}$ | $C_{14}$ | Na salt | 150–154 |
| 2b | 2 | 2 | $C_{14}$ | $C_{14}$ | $NH_4$ salt | 92–94 |
| 3a | 3 | 2 | $C_{14}$ | $C_{14}$ | Acid | 63 |
| 3b | 3 | 2 | $C_{14}$ | $C_{14}$ | K salt | 180 |
| 4a | 2 | 2 | $C_{16}$ | $C_{16}$ | Acid | 74–75 |
| 4b | 2 | 2 | $C_{16}$ | $C_{16}$ | K salt | 150–153 |
| 5a | 2 | 2 | $C_{18}$ | $C_{18}$ | Acid | 82–83 |

-continued

| Example No | X[1] | n | Y | Z | Salt/acid | m.p. (°C.) |
|---|---|---|---|---|---|---|
| 5b | 2 | 2 | C$_{18}$ | C$_{18}$ | K salt | 155–157 |
| 5c | 2 | 2 | C$_{18}$ | C$_{18}$ | NH$_4$ salt | 85–87 |
| 6 | 2 | 1 | C$_{10}$ | C$_{10}$ | Acid | 70–72 |
| 7a | 2 | 1 | C$_{14}$ | C$_{14}$ | Acid | 71–72 |
| 7b | 2 | 1 | C$_{14}$ | C$_{14}$ | K salt | 160–163 |
| 8a | 3 | 1 | C$_{14}$ | C$_{14}$ | Acid | 68 |
| 8b | 3 | 1 | C$_{14}$ | C$_{14}$ | K salt | 174–175 |
| 9a | 2 | 1 | C$_{16}$ | C$_{16}$ | Acid | 76–77 |
| 9b | 2 | 1 | C$_{16}$ | C$_{16}$ | K salt | 155–157 |
| 10 | 3 | 1 | C$_{18}$ | C$_{18}$ | Acid | 80–81 |
| 11a | 2 | 1 | C$_{18}$ | C$_{18}$ | Acid | 82–84 |
| 11b | 2 | 1 | C$_{18}$ | C$_{18}$ | K salt | 145–147 |
| 12a | 2 | 1 | C$_{18}$ | C$_{18}$ | Acid | 42–43 |
| 12b | 2 | 1 | C$_{18}$ | C$_{18}$ | K salt | (wax) |
| 12c | 2 | 1 | C$_{18}$ | C$_{18}$ | NH$_4$ salt | 42–43 |
| 13 | 2 | 2 | C$_{18}$ | C$_{18}$ | Acid | ≦25 (oil) |
| 13a | 2 | 2 | C$_{18}$ | C$_{18}$ | K salt | (wax) |
| 13b | 2 | 2 | C$_{18}$ | C$_{18}$ | Na salt | (wax) |
| 14a | 2 | 1 | C$_{22}$ | C$_{22}$ | Acid | 92 |
| 14b | 2 | 1 | C$_{22}$ | C$_{22}$ | K-salt | 122–126 |

The number of carbon atoms for Y and Z is stated in the Table. The radicals Y and Z are straight-chain and, with the exception of Examples 12 and 13, are saturated. Y and Z in Examples 12 and 13 are CH$_3$—(CH$_2$)$_7$—CH=CH—(CH$_2$)$_7$—.

Example of use

Encapsulation of a water-soluble dye (1) No. of carbon atoms in moiety 100 mg of the substance of Example 7b (K salt) were dissolved in 20 ml of diisopropyl ether. 1.0 ml of a 25 mM 6-carboxylfluoresceine solution (sodium salt in buffer solution: 0.9% of NaCl +10mM phosphate, pH 7.2) was added, after which the mixture was emulsified by treatment with ultrasound. The organic solvent was then carefully removed in a rotary evaporator, and the residue was dispersed with 10 ml of the abovementioned buffer solution by shaking in a water bath at 55° C. until a cloudy but homogeneous solution was obtained. After the solution had cooled, 1.0 ml of the solution was poured onto a gel filtration column (®Sephadex G 50 coarse, Φ 1.5 cm, length 11 cm, elution with buffer solution). The fraction first eluted contained the dye-containing vesicles. 100 μl of 10% strength aqueous ®Triton-x-100 solution were added to all fractions, the fractions were heated at 50°–60° C. for a short time and the extinction was then measured at 492 nm in order to determine the amount of encapsulated dye (as a percentage of the amount originally added). In the case described here, this value was 34±2%. When the dye was added only after vesicle formation (emulsion in buffer solution, addition of dye prior to gel filtration), a colorles vesicle fraction was obtained.

We claim:

1. A method for improving delivery and reducing toxicity of biologically active substances when administered to a subject, comprising:

encapsulating the active substance with an effective encapsulating amount of a compound of formula I:

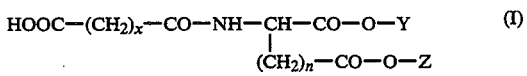

$$\text{HOOC—(CH}_2\text{)}_x\text{—CO—NH—CH—CO—O—Y} \quad \text{(I)}$$
$$| $$
$$\text{(CH}_2\text{)}_n\text{—CO—O—Z}$$

wherein Y and Z are, independently, an aliphatic hydrocarbon radical of 10 to 22 carbons atoms, x is 2 to 6 and n is 1 to 2; or a sodium, potassium or ammonium salt thereof, wherein said encapsulating is in a form selected from the group consisting of liposomes, emulsions, micelles and gels.

2. The method of claim 1, wherein Z is —(CH$_2$)$_8$—CH=CH—(CH$_2$)$_7$—CH$_3$.

3. The method of claim 1, wherein said encapsulating is in the form of a liposome.

* * * * *